(12) United States Patent
Anderson et al.

(10) Patent No.: US 7,011,093 B2
(45) Date of Patent: *Mar. 14, 2006

(54) MICROENCAPSULATED FRAGRANCES AND METHODS OF COATING MICROCAPSULES

(75) Inventors: Milton W. Anderson, Eagan, MN (US); Nobuya Hashizume, Plymouth, MN (US); Peter J. Cronk, Moorestown, NJ (US); Kristen Cronk, Moorestown, NJ (US)

(73) Assignee: CNS, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/419,387

(22) Filed: Apr. 21, 2003

(65) Prior Publication Data

US 2004/0005830 A1    Jan. 8, 2004

Related U.S. Application Data

(63) Continuation of application No. 09/541,960, filed on Apr. 4, 2000, now Pat. No. 6,550,474, which is a continuation-in-part of application No. 09/099,825, filed on Jun. 18, 1998, now Pat. No. 6,244,265, which is a continuation-in-part of application No. 08/942,797, filed on Oct. 2, 1997, now abandoned, which is a continuation of application No. 08/791,760, filed on Jan. 29, 1997, now Pat. No. 5,706,800.

(51) Int. Cl.
*A62B 7/00* (2006.01)

(52) U.S. Cl. .................. 128/206.12; 128/201.14; 128/202.17; 128/204.13; 128/206.18; 128/207.18; 128/204.14; 602/44; 602/45; 602/48; 602/49; 602/50; 602/51; 602/57; 606/199; 606/204.45; 428/40.1; 428/40.2; 428/343; 428/402; 428/402.2; 428/403; 428/542.6; 442/96

(58) Field of Classification Search ............... 428/40.1, 428/40.2, 41.8, 42.3, 343, 354, 402, 402.2, 428/403, 542.4, 543, 905; 442/43.45, 96, 442/123, 149, 151, 185, 286, 394, 400, 401; 128/201.14, 202.17, 204.13, 206.18, 200.24, 128/207.18, 204.14; 602/44, 45, 48, 49, 602/50, 51, 52, 57; 606/199, 204.45
See application file for complete search history.

(56) References Cited

U.S. PATENT DOCUMENTS 2,498,338 A    2/1950 Martin (Continued)

FOREIGN PATENT DOCUMENTS

EP    0161091    4/1986

(Continued)

OTHER PUBLICATIONS

European Search Report dated Apr. 16, 2003.

*Primary Examiner*—Ms. Arti R. Singh
(74) *Attorney, Agent, or Firm*—Duane Morris LLP

(57) ABSTRACT

Nasal dilators and strips, methods of their manufacture, and methods for improving the breathing of individuals are provided. The strips and dilators include an elongated substrate, with or without a dilating component or portion, having top and bottom surfaces and a pressure-sensitive adhesive disposed on the bottom surface. The dilator is designed to provide a gentle expanding force to the nasal wall tissue when the dilator is adhesively attached to the nose. This invention further includes a cosmetic fragrance, an aromatic medication and/or transdermal medication disposed on the strips or dilators. In order to improve the shelf-life and in-use olfactory effectiveness of such products, fragrance delivery mechanisms are used. Separation of volatile oils and adhesives are also provided to minimize adhesive residue.

17 Claims, 3 Drawing Sheets

U.S. PATENT DOCUMENTS

| | | |
|---|---|---|
| 2,736,721 A | 2/1956 | Dexter |
| 2,814,601 A | 11/1957 | Currie, et al. |
| 2,857,356 A | 10/1958 | Goodwin |
| 3,464,413 A | 9/1969 | Goldfarb et al. |
| 3,627,851 A | 12/1971 | Brady |
| 3,645,835 A | 2/1972 | Hodgson |
| 3,772,247 A | 11/1973 | Flannigan |
| 3,921,636 A | 11/1975 | Zaffaroni |
| 3,948,254 A | 4/1976 | Zaffaroni |
| 3,993,072 A | 11/1976 | Zaffaroni |
| 4,243,224 A | 1/1981 | Spector |
| 4,427,737 A | 1/1984 | Cilento et al. |
| 4,487,801 A | 12/1984 | Turnbull et al. |
| 4,493,869 A | 1/1985 | Sweeny et al. |
| 4,528,226 A | 7/1985 | Sweeny |
| 4,582,492 A | 4/1986 | Etter et al. |
| 4,654,256 A | 3/1987 | Doree et al. |
| 4,655,767 A | 4/1987 | Woodard et al. |
| 4,661,388 A | 4/1987 | Charbonneau |
| 4,675,009 A | 6/1987 | Hymes et al. |
| 4,738,984 A | 4/1988 | Parker |
| 4,774,133 A | 9/1988 | Doree et al. |
| 4,802,626 A | 2/1989 | Forbes et al. |
| 4,826,683 A | 5/1989 | Bates |
| 4,867,150 A | 9/1989 | Gilbert |
| 4,889,755 A | 12/1989 | Charbonneau |
| 4,898,633 A | 2/1990 | Doree et al. |
| 4,899,739 A | 2/1990 | Konishi |
| 4,927,631 A | 5/1990 | Bates |
| 4,951,657 A | 8/1990 | Pfister et al. |
| 4,952,400 A | 8/1990 | Tararuj et al. |
| 4,970,240 A | 11/1990 | Kielley |
| 4,988,577 A | 1/1991 | Jamieson |
| 5,018,974 A | 5/1991 | Carnahan et al. |
| 5,035,886 A | 7/1991 | Chakrabarti et al. |
| 5,071,645 A | 12/1991 | Johnson et al. |
| 5,114,735 A | 5/1992 | Rua, Jr. et al. |
| 5,114,979 A | 5/1992 | Kielley |
| 5,232,702 A | 8/1993 | Pfister et al. |
| 5,288,492 A | 2/1994 | Morris |
| 5,322,689 A | 6/1994 | Hughes et al. |
| 5,395,047 A | 3/1995 | Pendergrass, Jr. |
| 5,455,043 A * | 10/1995 | Fischel-Ghodsian ........ 424/448 |
| 5,459,157 A | 10/1995 | Stroppolo et al. |
| 5,478,565 A | 12/1995 | Geria |
| 5,533,499 A | 7/1996 | Johnson |
| 5,533,503 A | 7/1996 | Doubek et al. |
| 5,536,263 A | 7/1996 | Rolf et al. |
| 5,553,605 A | 9/1996 | Muchin |
| 5,562,908 A | 10/1996 | Geria |
| 5,681,577 A | 10/1997 | Lech et al. |
| 5,706,800 A | 1/1998 | Cronk et al. |
| 5,727,544 A | 3/1998 | Miura |
| 5,741,510 A | 4/1998 | Rolf et al. |
| 5,890,486 A * | 4/1999 | Mitra et al. ............ 128/200.24 |
| 6,090,403 A | 7/2000 | Block et al. |
| 6,092,521 A | 7/2000 | Miura |
| 6,183,770 B1 | 2/2001 | Muchin et al. |
| 6,244,265 B1 | 6/2001 | Cronk et al. |
| 6,261,593 B1 | 7/2001 | Muchin et al. |
| 6,276,360 B1 | 8/2001 | Cronk et al. |
| 6,295,982 B1 | 10/2001 | Reed, Jr. |
| 6,399,192 B1 | 6/2002 | Pinna et al. |

FOREIGN PATENT DOCUMENTS

| | | |
|---|---|---|
| EP | 0195254 | 4/1986 |
| EP | 1033118 | 9/2000 |
| JP | 7-48250 | 2/1995 |
| JP | 7048250 A | 2/1995 |
| JP | 7215847 A | 8/1995 |
| JP | 10120555 A | 5/1998 |
| WO | WO92/14607 | 9/1992 |
| WO | WO93/13938 | 7/1993 |
| WO | WO95/26155 | 10/1995 |
| WO | WO98/06360 | 2/1998 |
| WO | WO98/57613 | 12/1998 |
| WO | WO99/65430 | 12/1999 |

* cited by examiner

MICROENCAPSULATED FRAGRANCES AND METHODS OF COATING MICROCAPSULES

RELATED APPLICATION DATA

This application is a continuation of application Ser. No. 09/541,960, filed on Apr. 4, 2000 now U.S. Pat. No. 6,550,474, which is a continuation-in-part of application Ser. No. 09/099,825 filed Jun. 18, 1998, now U.S. Pat. No. 6,244,265, which is a continuation-in-part of application Ser. No. 08/942,797 filed Oct. 2, 1997, abandoned, which is a continuation of application Ser. No. 08/791,760, filed Jan. 29, 1997, now U.S. Pat. No. 5,706,800.

FIELD OF THE INVENTION

This invention relates to nasal strips, methods of their manufacture and method of easing the breathing of patients, and more particularly to adhesive-backed nasal strips containing fragrances.

BACKGROUND OF THE INVENTION

The nose has the important function of first contact with inspired air. This air is laden with pollutants, suspended material, microbes, and noxious substances. Air can be cold and dry and often needs warming and humidification before entering the lower respiratory tract. The nose also serves as a sensitive detector of air-borne chemicals and helps sense the flavor of food and drink. The nose further serves an important role in the immune system because it is the first site of contact of many air-borne allergens with the body's defense system.

Many people have difficulty breathing through their nose. Some causes for restricted breathing are congestion of the nasal lining from allergies, deviation of the nasal septum, i.e., the partition between the two nostrils, which narrows one or both nasal chambers, or by a droopy nasal tip.

During exercise, nasal breathing becomes more difficult and some people are forced to open their mouths to get enough air. When exercising, it is necessary to breath rapidly. Upon rapid breathing, a negative pressure is created in the nasal chamber forcing the lower sides of the nose to collapse which obstructs breathing. If nasal breathing becomes obstructed, it is necessary to breath through the mouth in order to obtain an adequate amount of air. When a person becomes a mouth breather, the important functions of the nose are bypassed.

The nose accounts for approximately half of the total airway resistance to airflow. Nasal obstruction can contribute to an increase in snoring and sleep apnea frequency and severity. Snoring sounds have been associated with increased upper airway occlusion. Upper airway narrowing, collapsibility and resistance are recognized factors contributing to snoring and obstructive sleep apnea.

The nose is often affected by allergies, the flu or a cold. The common cold, although not usually a serious illness, is a highly prevalent, discomforting and annoying affliction. The term is applied to minor respiratory illnesses caused by a variety of different respiratory viruses. While rhinoviruses are the major known cause of common colds, accounting for approximately 30 percent of colds in adults, viruses in several other groups are also important. While immune responses occur, and infection with some respiratory tract viruses therefore could be prevented by a vaccine, developments of a polytypic vaccine to cover all possible agents is impractical. Thus, the problem of controlling acute upper respiratory disease presents complex challenges, and the long-desired discovery of a single cure for the common cold is an unrealistic expectation.

Early symptoms may be minimal with only mild malaise, sore throat and nasal complaints. With rhinovirus infection, symptoms of nasal discharge, nasal congestion, and sneezing usually commence on the first day of illness and progress to maximum severity by the second or third day. Along with nasal symptoms may come sore, dry or scratchy throat and hoarseness and cough. Other symptoms may include mild burning of the eyes, loss of smell and taste, a feeling of pressure or fullness in the sinuses or ears, headache, and vocal impairment. Fever can occur, but is uncommon. Influenza infection generally includes fever, often of sudden onset and persisting for several days, and with great severity; generalized aches and pains; fatigue and weakness; and chest discomfort.

The costs of treating colds with over-the-counter medications in the United States is estimated at an annual cost of over 1.5 billion dollars. The direct costs of treatment in outpatient clinics is estimated at almost four billion dollars. Indirect costs, based on amount of lost wages because of restricted activity are substantially higher.

At present, only symptomatic treatment is available for the common cold; the majority of these drugs are taken orally. Exemplary prior art oral compositions for the treatment of cough, cold, cold-like and/or flu symptoms and the discomfort, pain, fever and general malaise associated therewith generally contain an analgesic (aspirin or acetaminophen) and one or more antihistamines, decongestants, cough suppressants, antitussives and expectorants. For individuals with certain medical conditions such as heart disease, hypertension, diabetes or thyroid disorders, oral drugs such as decongestants could pose a risk of unfavorable drug interactions and may cause an adverse reaction. It would, therefore, be highly desirable to deliver relief from these symptoms via topical compositions and thus without the need to orally ingest drugs. In addition, topical colds medications are less likely to cause drowsiness or other side effects associated with oral decongestants.

Nasal dilators have been suggested for aiding breathing through the nose during snoring, athletic events, and for treating the symptoms of the common cold or flu. There have been traditionally two types of dilators which have been effective in humans. One type uses small rings or cages connected to a resilient structure. The rings are inserted into each nasal passage while the resilient structure spreads to provide unobstructed breathing. These dilators have been criticized because they are often uncomfortable to wear. Since the cages or rings are inserted into contact with sensitive nasal tissue, they have been known to cause irritation and itching. Such devices are disclosed in U.S. Pat. No. 3,710,799 to Caballero and the NOZOVENT dilator disclosed in Petruson D310,565.

More recently, advancements have been made in nasal dilators which attach to the outer wall tissue of the nose and aid in preventing the inner nasal tissue from drawing in during breathing. Such dilators include a flexible strip of material adhesively attached to a substrate. The dilator is fastened to the nose and the resilient material acts to keep the left and right nasal passages from drawing in or collapsing during inhalation. This usually occurs due to a malformation, such as a deviated septum or due to swelling during allergic reactions and the like. Examples of nasal dilators which are adhesively attached to the outer skin of a human nose are disclosed in Doubek et al., U.S. Pat. No. 5,533,503 and Muchin, U.S. Pat. No. 5,546,929.

In related application U.S. Pat. No. 5,706,800, which is hereby incorporated by reference, there is disclosed a medicated nasal dilator including essential fragrance oils, such as camphor and menthol. Such fragrance oils are commonly used in the treatment of nasal congestion, bronchial asthma and cough suppression. They are widely available in the form of hard confection drops, nasal sprays and inhalers. The '800 patent discloses a medicated nasal dilator having a resilient layer or portion which helps to provide mechanical dilation while the incorporated fragrance introduces an aromatic substance, preferably a medication, for treating the patient's symptoms.

Early attempts to produce medicated dilators have uncovered several shortcomings that need to be addressed. Aromatic substances, such as menthol and camphor, while therapeutically effective, are highly volatile. Oil-base carriers, such as petrolatum, commonly called petroleum jelly, while effective in containing volatile menthol and camphor in airtight containers, quickly release these oily substances into the atmosphere when exposed to air. Accordingly, nasal dilators impregnated with fragrance oils generally lose their odor quickly because the scent dissipates during the shelf life of the product.

Although hermetic foil packaging has been discussed, scented dilators remain relatively stable only until the packaging is opened. Without individually wrapping each dilator, the remaining scented dilators dissipate their oils quickly. Separately packaging each dilator in its own hermetic packaging may improve shelf life, but it increases the expense of the product and makes it generally more inconvenient to use due to the tenacious materials, such as mylar, etc., used to make hermetic packaging. Additionally, such packaging fails to improve upon the in-use duration of the fragrance when exposed to perspiration, body heat, dirt and dust, and the time demands of a full night's sleep.

Another drawback associated with scented dilators is the tendency of the nasal nerve endings to become desensitized to the fragrance, long before the fragrance has dissipated from the product. Due to the extended periods of time for which nasal dilators and strips are recommended, from an hour to 12 hours, prolonged exposure to the same volatile oil or mixture, such as menthol or camphor, generally engenders a phenomena of adaptation called "olfactory saturation", which results in a gradual loss of smell of the active fragrance to the wearer. This, of course, is a distraction to wearers, who may feel the need to replace the dilator with a fresh product, only to find that a new dilator fails to completely refresh the olfactory impression.

Fragrance oils are also known to break down the structure of known pressure-sensitive adhesives used to attach nasal dilators to skin, such as polyacrylate or polyvinylethyl ether blend adhesives. Such fragrances tend to migrate to the adhesive layer, even when they are incorporated into the fabric substrate. When fragrance oil mixes with the adhesive, it plasticizes the adhesive, making it less cohesive and more sticky. The internal strength of the adhesive is reduced considerably. This can have the unfortunate, unintended effect of causing a nasal dilator, which is already exerting release pressure due to resilient members contained therein, to completely remove its adhesive attachment from the nose. To make matters worse, when it is desired to remove the dilator or strip, portions of the plasticized adhesive remain on the skin surface, leaving it tacky and unsightly.

There also remains a concern relating to the proper dosage of fragrance oils used for nasal dilators and strips. If the fragrance oil concentration is too high, it can irritate the eyes causing tears. If the dosage is too low, there is insufficient fragrance to produce an olfactory effective amount, which, in the case of cosmetic fragrances, makes the product less appealing to the consumer, and in the case of medicated aromatics, renders these devices therapeutically ineffective.

Accordingly, there remains a need for improved nasal dilators and strips which incorporate fragrances, transdermal medications and other ingredients. Such products remain an emerging technology, requiring innovation to overcome the problems associated with short fragrance shelf life and in-use effectiveness, olfactory saturation, adhesive residue and dosage issues.

SUMMARY OF THE INVENTION

This invention provides improved nasal strips and nasal dilators which contain aromatic substances and improvements for extending the olfactory effectiveness of fragrances, overcoming olfactory saturation, minimizing adhesive residue and generally improving the delivery of an olfactory effective amount of a fragrance, transdermal or aromatic medication.

In the first embodiment of this invention, a medicated nasal strip is provided which contains an elongated flexible layer sized to comfortably fit across a bridge of a nose, a pressure-sensitive adhesive layer disposed on the bottom surface of the flexible layer, and an aromatic substance disposed on a portion of the nasal strip in an olfactory effective amount. The nasal strip further contains extended release means for extending the useful life of the aromatic substance.

In a further embodiment of this invention, a nasal strip is provided which contains an elongated flexible layer and a bio-compatible, pressure-sensitive adhesive disposed on a bottom surface of this layer. The nasal strip further includes an aromatic substance disposed on the nasal strip so as to avoid substantial contact and mixing with said pressure-sensitive biocompatible adhesive layer.

In a further embodiment of this invention, a nasal strip is provided which includes an elongated flexible member, bio-compatible pressure-sensitive adhesive layer and an aromatic substance. This strip further includes a dual fragrance delivery system for minimizing olfactory saturation by the wearer.

Accordingly, this invention provides solutions to the problems encountered in the early development of medicated nasal dilators and strips. In an effort to improve neat shelf life and dissipation of fragrance oils or essential oils during use, this invention includes extended release means, including such individual fragrance delivery mechanisms as fixatives, gels, starches, carriers, porous hydrophilic inorganics, micro-capsules, cellulosic carriers, cyclodextrine coatings and body-activated coatings, such as those which release fragrant oils upon achieving a certain temperature, reaching a certain pH, or, when they come in contact with liquid perspiration. The fragrance delivery mechanisms of this invention help to contain the essence of the volatile aromatic compounds over a greater period of time to extend the shelf life, and increase the in-use olfactory effectiveness. Additional means for overcoming olfactory saturation are provided which include at least two different fragrance delivery systems and/or at least two different fragrances (or a fragrance and a transdermal medication). The different delivery systems can deliver an aromatic drug, transdermal drug, or fragrance under different use conditions, or at different times during use to keep the product fresh to the wearer. For example, re-encapsulation can be used to release and preserve fragrance oils or transdermal medications during the occurrence and evaporation of perspiration during athletic events, or the rise and fall of body temperature, caused by viral infections or flu symptoms.

Additional improvements of this invention include separation layers and nasal strip designs for minimization of mixing contact between pressure-sensitive adhesives and fragrance oils in order to avoid adhesive breakdown and the resulting residue left on nasal skin. Methods of manufacturing nasal strips and dilators, as well as their use are also described.

BRIEF DESCRIPTION OF THE DRAWINGS

The accompanying drawings illustrate preferred embodiments of the invention as well as other information pertinent to the disclosure, in which.

DETAILED DESCRIPTION OF THE INVENTION

This invention provides adhesively-applied nasal strips and dilators and methods for substantially preventing a nasal wall tissue of a nose from drawing in during breathing. As used herein, the following terms are defined:

"aromatic medication" refers to therapeutic substances and compounds which can be consumed by inhaling through the nose, such as a medicated vapor or gas, which have potential or demonstrated efficacy;

"medicated" and "medicine" will be used broadly to connote the inclusion of any of a variety of treatments including aromatic, topical and transdermal medicines, anti-viral, anti-microbial or anti-bacterial agents, scents, salves and other therapeutic substances which might be desirable on tissues as discussed herein;

"neat" refers to a fragrance either in its undiluted or unused condition. It can refer to the fragrance on a dilator strip as it is packaged and ready for a wearer to apply to his or her skin, or it can be used to define a relatively pure fragrance prior to adding/mixing other fragrances and/or substances.

"in-use" refers to use by a patient or a consumer in its commercially-intended fashion;

"extended release" refers to a group of substances, compounds, and/or devices useful for sustained release of fragrances to increase either the neat or in-use olfactory effectiveness or useful life.

"fragrance oil" refers to the numerous known oil-based scents, their homologues, derivatives and chemical variations.

"body activated" means that the activity of the cosmetic fragrance, aromatic or transdermal medication increases when applied to the body. This can be accomplished by means of pH, heat or perspiration activation, for example.

"fragrance notes" means fragrance ingredients blended or in neat form which achieve "top", "middle", or "bottom" note components. The first is a refreshing quality sensed upon application. The last is the essence of the fragrance which stays with the wearer for a long time. The middle note is the perceived quality that bridges from top to bottom note. These materials themselves are each classified with respect to the aromas given off, as to providing a green note, floral note, aldehidic note, fruity note, chypre note, oriental note, leather note, tobacco note, etc.

"dual fragrance delivery system" refers to either dual fragrances, dual notes, or dual delivery mechanisms for extending the olfactory effectiveness of fragrances and aromatic medications. Such delivery mechanisms include, for example, fixatives, gels, starches, microcapsules, fragrance carriers, pH sensitive compounds, waxy substances, polymers, cyclodextrins, cellulose, and variations thereof.

Nasal Dilator

Figure 1:
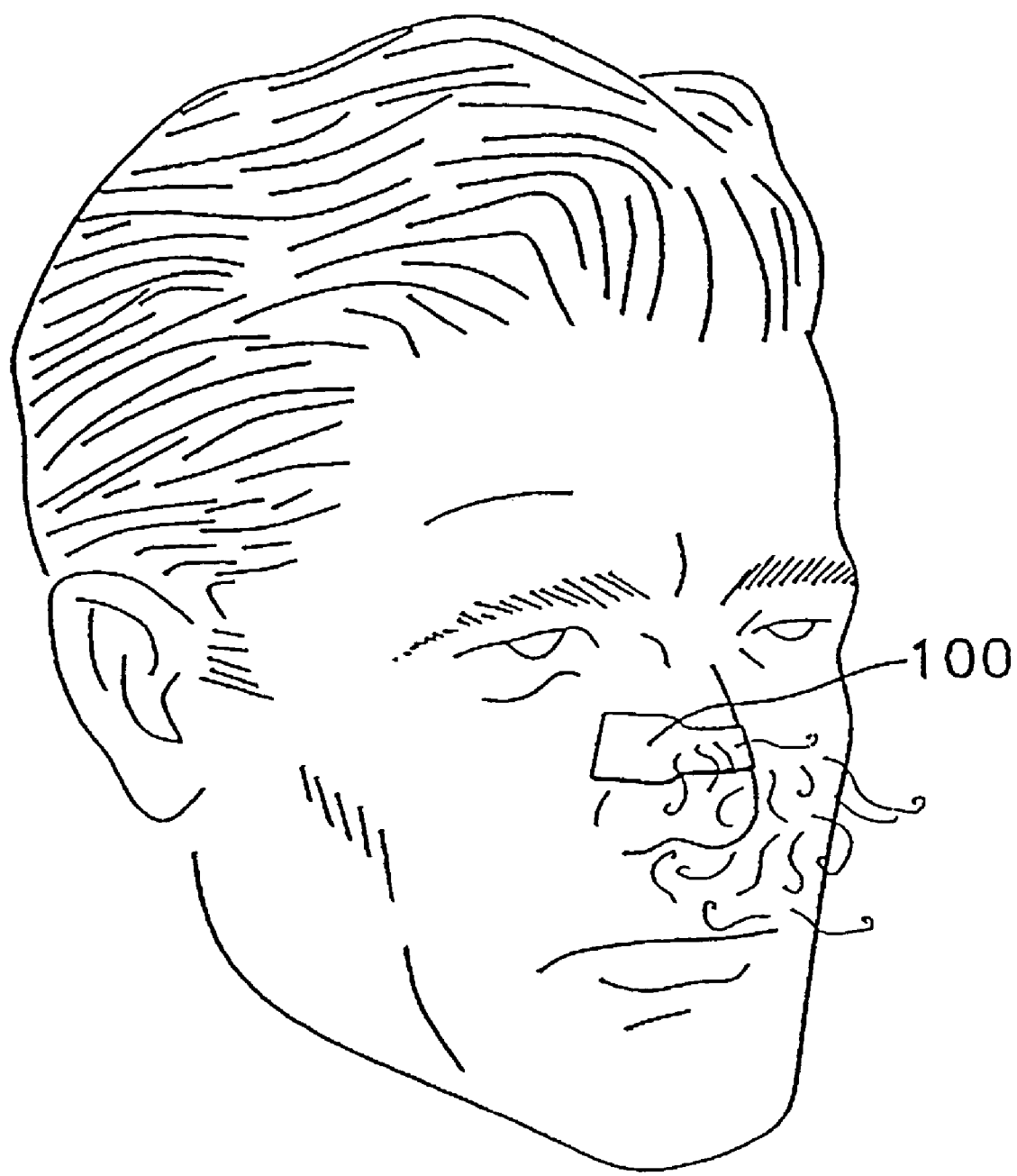
FIG. 1: is a partial front perspective view of a man wearing the preferred nasal dilator of this invention.
Figure 2:
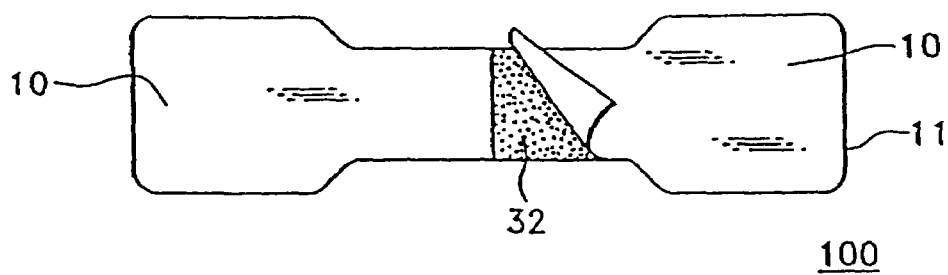
FIG. 2: is a top planar view of a preferred nasal dilator of this invention with a partial peel back view of the adhesive layer.
Figure 3:
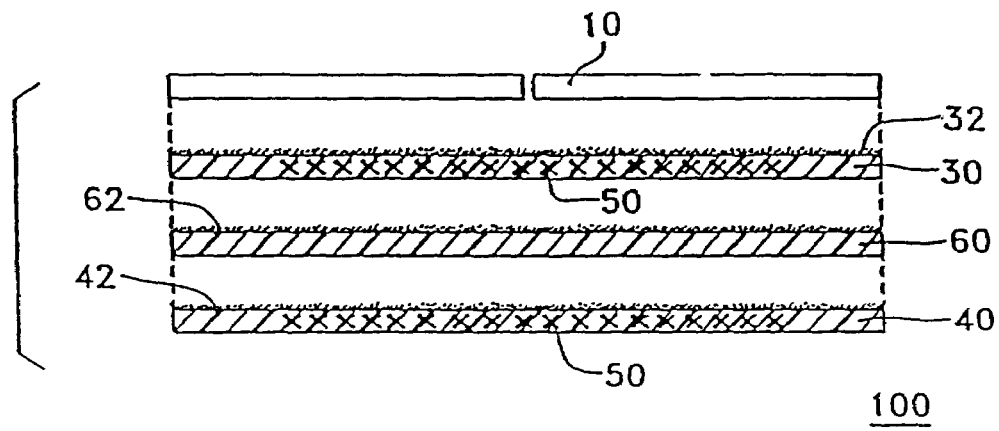
FIG. 3: is a side elevation, cross-sectional, exploded view of the nasal dilator of FIG. 2.
Figure 4:
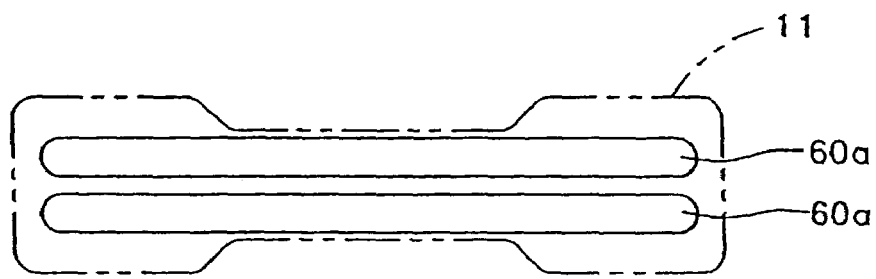
FIG. 4: is a top planar view of a preferred resilient member, including the periphery of the substrate of the nasal dilator in phantom.

With reference to the figures and in particular, FIGS. 1–3 thereof, there is shown a preferred nasal dilator 100 sized to fit across the nose of the wearer so as to engage the outer wall tissue of the left and right nasal passages of the wearer. As shown in FIGS. 2–3 the nasal dilator 100 includes an elongated substrate 30 having a pair of longitudinal sides, a pair of transverse ends and top and bottom surfaces thereon. Disposed on a bottom surface of the substrate 30 is an adhesive layer 32 for permitting easy attachment to the wearer's skin. Also attached to the substrate is a resilient member 60 which provides a gentle expanding force to the nasal wall tissue when the dilator is adhesively attached to the nose. Finally, an aromatic substance 50 is disposed on a portion of the dilator so as to be inhaled through the nose of the wearer during breathing. Additionally, a transdermal substance can be added to the bottom surface of the dilator 100, with, or without an aromatic substance, such as a fragrance or aromatic medication.

In further embodiments of this invention, the dilator 100 can include a backing layer 40. The backing layer 40 and resilient member 60 are desirably bonded to the substrate 30 using pressure sensitive adhesive layers 42 and 62. As shown in FIG. 3 the aromatic substance 50 can be disposed on any surface of the dilator 100. Preferably the aromatic substance 50 is disposed on an absorbent layer portion of the dilator 100. The absorbent layer portion can be a separate absorbent layer or a portion of the elongated substrate 30 or backing layer 40, for example. Alternatively, the aromatic substance 50 can be disposed in one of the adhesive layers in an admixture or segregated form, such as in a separate bottom layer location, or contained within fragrance carriers, microcapsules, or coatings, for example. Finally, a release paper strip 10, such as silicone or wax coated kraft paper, can be added over the pressure sensitive adhesive layer 32 prior to packaging the dilator 100 for sale.

The elongated substrate 30 of this invention may include any thin, flexible, breathable material for maximizing comfort. Preferably this material permits the passage of air and moisture vapor, such as perspiration, but inhibits the passage of dirt and liquid perspiration or rain water, etc. The elongated substrate can include, for example, a woven or non-woven fabric material, such as non-woven, polyester fabric. One good example is a fabric produced by DuPont E. I. de Nemours & Co., Inc. under the trademark Sontara®. Alternatively, the elongated substrate 30 can include a thermoplastic woven or non-woven fabric, such as spun-bonded, or melt-blown, polyethylene or polypropylene fibers, which in sufficient thickness can be "self-resilient," or capable of gently opening nasal passageways when adhesively applied to exterior nasal tissue, as discussed in more detail below. The substrate 30 can also be treated with the aromatic medication 50 of this invention, along with a hydrophilic or hydrophobic additive for absorbing or repelling sweat or moisture on a selective basis.

Attached to the substrate 30 on the nose skin-facing side, or bottom surface, of the substrate 30 is an adhesive layer 32. This adhesive layer, along with optional adhesive layers 62 and 42 can be made of a pressure sensitive, hypoallergenic, biocompatible adhesive material. As used herein, "pressure-sensitive" refers to any releasable adhesive or releasable tenacious means. Adhesive compositions suitable for nasal dilators and nasal strips include water-based pressure-sensitive adhesives, such as acrylate adhesives, thermoplastic "hot melt" adhesives, two-sided adhesive tape, elastomer-based adhesives, and acrylic adhesives. Good examples include polyacrylate adhesive, polyvinylethyl ether blend adhesive, and 3M1509 double-sided medical tape provided by 3M Inc., St. Paul, Minn. The 3M product is a double-sided transparent polyethylene film, coated on both sides with a hypoallergenic, pressure-sensitive acrylate adhesive, supplied on a paper liner. Of course, adhesive layers 62 and 42 need not be a pressure-sensitive type at all, since once the resilient member 60 and backing layer 40 are adhered to the substrate 30, it is undesirable for these layers to separate during application or removal of the dilator from the nose.

The resilient member 60 of this invention preferably includes one or more spring strips 60a which can be die-cut from spring ribbon material. Good examples of spring ribbon material include biaxially oriented polyester that is approximately 0.01–0.15 inches thick, but polyethylene or polypropylene strips of like or greater thickness would also provide expanding force to the dilator 100.

Figure 5:
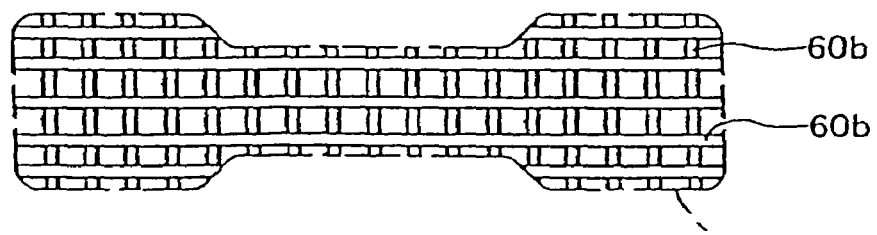
FIG. 5: is a top planar view of an alternative resilient member consisting of a reinforcing scrim also depicting the periphery of the substrate in phantom.

Although both an elongated substrate 30 and resilient member 60 are disclosed, there is no reason why the functions of these members cannot be performed by a single elongated resilient member, or layer, comprising a flexible, but spring-like, woven oriented layer, non-woven layer, scrim, ribbon composite or sheet material. For example, a non-woven web of melt-blown or spun-bonded fibers of polyethylene or polypropylene, cut into a strip of about 0.01–0.15 inches thick by about 2–4 inches in length would transmit air and perspiration vapor easily, and would also provide a spring force to gently open nasal openings when adhesively applied to a nose. Alternatively, as shown in FIG. 5, a resilient layer, such as scrim 60b can be disposed within, or substantially along the perimeter 11 of the substrate 30 or outer peripheral region of the dilator 100.

Fiber additions to the resilient member 60, such as glass, graphite, resin, carbon or boron will also improve resiliency. Resin fibers can include a variety of thermoplastic or thermosetting polymers. Good fiber candidates include, for example, nylon, polyethylene, and polyester fibers, for example SPECTRA or COMPET fibers sold by Allied Signal Corp., Kevlar® 29, 49 or 149 aramid fibers sold by DuPont, glass, such as E-glass and S-Glass fibers, graphite fibers, carbon fibers, boron fibers, or combinations of these fibers.

The resilient member, whether including spring strips 60a or a resilient scrim 60b or woven, non-woven, or solid film sheet layer (not shown) is preferably joined together in a webbing operation either by melt bonding, adhesive bonding or ultrasonic bonding. In conventional operations, a ribbon of resilient material and substrate material are adhesively joined together as they are fed into an overlapping position in a die or roller. Adhesive layers 42 and 62 are used to join the backing layer, resilient member 60 and elongated substrate 30 together prior to die-cutting to form the final periphery 11 of the dilator 100. The adhesive layers 42, 62 and 32 can be applied by spray, roll or knife, as is customary in the web-processing industry.

An important advantage of the resilient layer, such as scrim 60b or a sheet layer, as opposed to a pair of discrete spring strips 60a of this invention, is the elimination of a careful placement operation prior to die-cutting. Such an expensive step becomes unnecessary, since the resilient layer preferably conforms generally to the perimeter 11 of the final die-cut dilator. This can eliminate waste and minimize much of the expense of the webbing operation. It also provides for a more uniform spring action along most or all of the surface area of the dilator 100.

Additionally, this invention contemplates employing thermoplastic materials in the backing layer 40 and substrate 30, and alternatively, with respect to the resilient member 60 or layer. When thermoplastic materials are used, this invention enables inexpensive melt-bonding of the layers of material, with heat and pressure, to provide a composite nasal dilator structure. Melt-bonding could eliminate the need of additional adhesive layers 42 and 62 and provide a greater structural integrity to the dilator no matter what form of resilient member is employed. However, a woven layer, non-woven layer or resilient scrim 60b would ideally be suited for thermoplastic bonding of layers since these materials have pores for permitting softened thermoplastic material to bond between the fibers or filaments, further increasing the strength of the dilator 100.

Nasal Strip

Figure 6:
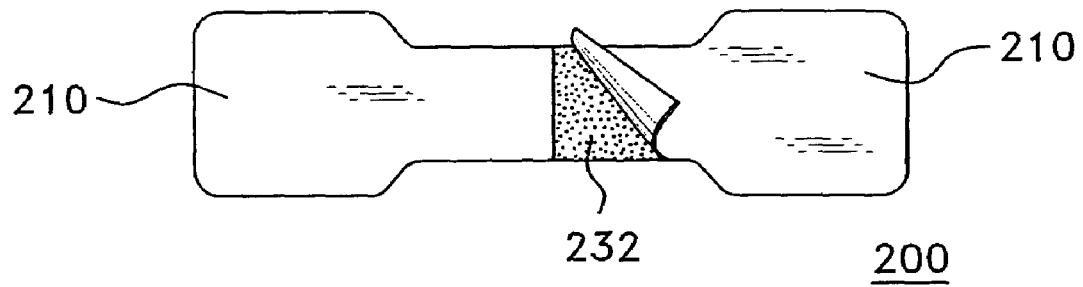
FIG. 6: is a top planar view of a preferred nasal strip of this invention with a partial peel-back view of the adhesive layer.
Figure 7:
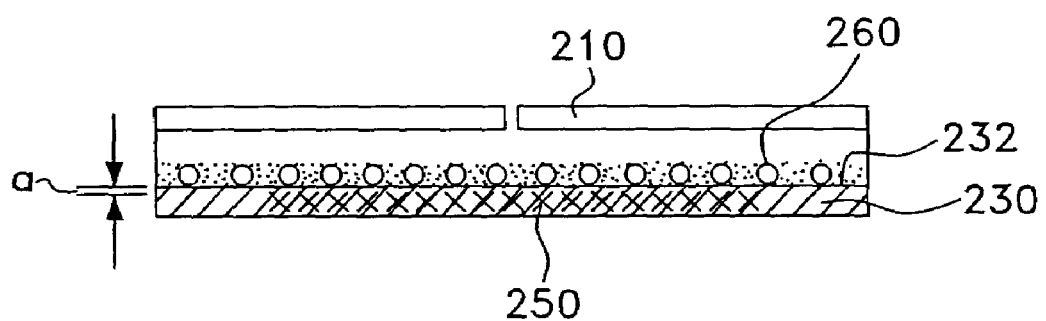
FIG. 7: is a side elevation, cross-sectional, exploded view of the nasal strip of FIG. 6.

As illustrated in FIGS. 6 and 7, there is further shown a nasal strip 200 which includes an elongated substrate 230, which may be a flexible fabric-like member, as discussed above for elongated substrate 30, or a resilient member which is self-resilient, and can permit a gentle expanding force to a nasal tissue when it has adhesively attached to a nose. In the preferred embodiment, however, the nasal strip 200 is merely a tape-like means for delivering a cosmetic fragrance, aromatic medication or transdermal medication. Fragrances and medications, hereinafter "active ingredient (s)", can be disposed in the elongated substrate 230, such as by absorption of active ingredients 250 into a fabric or pores of an absorbent layer, or by coating a top or bottom surface of one layer of the nasal strip 200, such as the elongated substrate 230.

Preferably the active ingredient 250 is separated by a separate layer, or layer portion, from the adhesive layer 232 facing the skin of the wearer, such as defined by dimension "(a)" in FIG. 7. This has the advantage of permitting neat fragrances, such as volatile oils, to be disposed onto the top of the elongated substrate 230 without risking the polymerization of the pressure-sensitive adhesive 232.

Alternatively, the elongated substrate 230, itself, can be made of a liquid or oil-resistant material, or treated to be hydrophilic on one side. Good examples include a woven or non-woven layer of thermoplastic or thermosetting fibers, or a solid thermoplastic or thermosetting film, which will enable an active aromatic ingredient to be disposed on an opposite planar surface from the pressure-sensitive adhesive 232, so as to keep them separate and minimize polymerization of the adhesive. Alternatively, as will be described below, fragrance oils and medications can be disposed within a fragrance delivery mechanism, such as a carrier 260. Although the carrier-entrapped oil or medication can be disposed anywhere on the substrate 230, the inherent property of most commercial carriers permit them to be disposed within the adhesive layer 232 without substantially mixing with the degradable polymers of the adhesive. Alternatively, microcapsules can be used in this fashion. Attached over the pressure-sensitive adhesive layer is a preferred release paper strip 210, similar to release paper strip 10.

The above nasal strip 200 can be modified by applying a 2-sided medical tape, such as the previously disclosed 3M1509 tape, or barrier layer of about 0.025–0.125 mm of an occlusive polyethylene film, such as disclosed in U.S. Pat. No. 4,880,690 to Szycher, and hereby incorporated by reference. A thermoplastic or thermosetting layer can separate the pressure-sensitive adhesive 232 and any fragrance oils or liquid medications in neat form which absorb through the substrate 230.

It is understood that these techniques have equal utility in the fabrication of nasal dilators. If the separating, thermoplastic or thermosetting film or fabric is of sufficient thickness, and tensile strength, it could also provide a resilient force for helping to gently open nasal passageways when adhesively applied to a nose. This could permit the use of a single layer to accomplish two functions, and help to reduce costs.

Fragrances and Aromatic Medications

Fragrance formulation is an art in which the senses of the skilled perfumer are more important than chemical analysis. A fragrance results from a variety of components or ingredients in a fragrance composition. Ordinarily, fragrances are created by blending materials comprising odoriferous essential oils, extracts from woods, gums, flowers and other botanicals, resins, animal secretions, and synthetic aromatic materials. These materials are blended in order to achieve what is known as top, middle and bottom notes. (See previous definition.)

Suitable fragrance compounds and compositions for this invention are disclosed in U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of said patents being incorporated herein by reference.

Fragrances can be classified according to their volatility. The highly volatile, low boiling, ingredients typically have boiling points of about 250° C. or lower. The moderately volatile ingredients are those having boiling points of about 250° C. to about 300° C. The less volatile, high boiling, ingredients are those having boiling points of about 300° C. or higher. Many of the fragrance ingredients as discussed hereinafter, along with their odor and/or flavor characters, and their physical and chemical properties, such as boiling point and molecular weight, are given in "Perfume and Flavor Chemicals (Aroma Chemicals)" Steffen Arctander, 1969, incorporated herein by reference.

Examples of the highly volatile, low boiling, fragrance ingredients, also called "top notes," are: anethole, benzaldehyde, benzyl acetate, benzyl alcohol, benzyl formate, iso-bornyl acetate, camphene, cis-citral (neral), citronellal, citronellol, citronellyl acetate, para-cymen, decanal, dihydrolinalool, dihydromyrcenol, dimethyl phenyl carbinol, eucalyptol, geraniol, geranyl acetate, geranyl nitrile, cis-3-hexenyl acetate, hydroxycitronellal, d-limonene, linalool, linaool oxide, linalyl acetate, linalyl propionate, methyl anthranilate, alpha-methyl ionone, methyl nonyl acetaldehyde, methyl phenyl carbinyl acetate, laevomenthyl acetate, menthone, iso-menthone, myrcene, myrcenyl acetate, myrocenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile ingredients. For example, lavandin contains as major components: linalool; linalyl acetate; geraniol; and citronellol. Lemon oil and orange terpenes both contain about 95%of d-limonene.

Examples of moderately volatile fragrance ingredients, also called "middle notes," are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethy Icitrate, vanilla and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients, referred to as "bottom notes, " are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

The fragrance employed in the nasal strips and dilators of the present invention can also comprise a cooling agent or a combination of cooling agents. See U.S. Pat. No. 5,725,865 to Mane et al., hereby incorporated by reference. Cooling agents are compounds which directly effect those nerve endings responsible for hot or cold sensations. In this sense, they are deemed to be medications. Suitable cooling agents are menthol, menthol-based or acyclic carboximides, and menthol-based or acyclic ketals (acetals). Suitable cooling agents useful in the present invention include: monomenthyl succinate and its alkali metal salts and alkaline earth derivatives, 3-1-menthoxypropane-1,2-diol, N-substituted-p-menthane-3-carboxamides and acyclic carboxamides and mixtures thereof, as disclosed in U.S. Pat. No. 5,622,992 to Beck, and hereby incorporated by reference.

Additional cooling agents include, for example, 3-1-menthoxy propane 1,2-diol, which is fully described in detail in U.S. Pat. No. 4,459,425, issued Jul. 10, 1984 to Amano et al., incorporated herein by reference in its entirety. This volatile aromatic is commercially available, as TK-10 from Takasago Perfumery Co., Ltd., Tokyo, Japan.

The N-substituted-p-menthane-3-carboxamides cooling agents are fully described in U.S. Pat. No. 4,136,163 to Watson et al., issued Jan. 23, 1979 incorporated herein by reference in its entirety. Preferred cooling agents of this class include N-ethyl-p-menthane-3-carboxamide, which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred cooling agent of this class is N,2,3-trimethyl-2-isopropylbutanamide which is commercially available as WS-23 from Wilkinson Sword Limited.

Preferred for use herein is a mixture of 3-1-menthoxy propane 1,2-diol, N-ethyl-p-menthane-3-carboxamide and N,2,3-trimethyl-2-isopropylbutanamide.

Various other non-active, aromatic components (e.g., aldehydes and esters) may also be used to impart fruit scents. These aromatics include, for example, benzaldehyde (cherry, almond); citral (lemon, lime); neral; decanal (orange, lemon); aldehyde C-8, aldehyde C-9 and aldehyde C-12 (citrus fruits); tolyl aldehyde (cherry, almond); 2,6-dimethyl-octanal (green fruit); and 2-dodecenal (citrus, mandarin). Mixtures of these aromatics can also be used.

Preferred examples of aromatic medications of this invention include camphor, ephedrine, eucalyptus oil, peppermint oil, menthol, methyl salicylate, bornyl acetate, lavender oil, or a combination of these. Menthol, because of therapeutic benefits which extend beyond its peppermint smell, is especially attractive as an antitussive, cooling agent and decongestant.

These and other aromatic active components are more fully described in 53 Federal Register 30561, Aug. 12, 1988, incorporated by reference herein.

Other Pharmaceutical Active Ingredients

Other pharmaceutical actives useful in the present invention include any chemical material or compound suitable for topical administration; however, such drugs should avoid interfering with the stability of the adhesive composition, if added thereto. Such substances include, but are not limited to antibiotics, wound healing agents, vasodilators, coagulants, birth control drugs, cardiovascular drugs, chemotherapeutic agents, vitamins, antiviral agents, antimicrobial agents, analgesics, anti-inflammatory agents, such as steroidal agents, such as hydrocortisone and triamcinolone, or non-steroidal agents, such as ibuprofen, naproxen, flufenamic acid, mefenamic acid, meclofenamic acid, prioxicam and felbinac. Transdermal decongestants and antihistamines are also available, such as diphenhydramine and triprolidine transdermal antihistamine, available from Proctor and Gamble Co., Inc., Cincinnati, Ohio; others include ephedrine (which can also be an aromatic), dimethindene, epinastine, emedastine, and clonidine. Transdermal substances can be delivered in a number of known manners.

Useful anesthetic or antipruritic drugs are selected from the group consisting of lidocaine, lidocaine hydro-chloride, bupivacaine hydrochloride, chloroprocaine hydrochloride, dibucaine hydrochloride, etidocaine hydrochloride, mepivacaine hydrochloride, tetracaine, tetracaine hydrochloride, dyclonine hydrochloride and hexylcaine hydrochloride, benzocaine, benzyl alcohol, butamben picrate, camphor (also an aromatic active), camphorated metacresol, dibucaine, dibucaine hydrochloride, dimethisoquin hydrochloride, diphenhydramine hydrochloride, juniper tar, menthol (also an aromatic medication), phenol, phenolate sodium, promazine hydrochloride, resorcinol and mixtures thereof.

Vitamins

Various vitamins may also be included in the topical compositions of the present invention. For example, Vitamin A, and derivatives thereof, ascorbic acid, Vitamin B, biotin, pantothenic acid, Vitamin D, and mixtures thereof may be used. Vitamin E, tocopherol acetate and derivatives may also be used.

These topical, aromatic and transdermal substances and medications can be added to the substrate 30, resilient member 60, mixed within adhesive layers 62, 42 or 32, as in, for example, a dispersion-type transdermal patch formulation made from acrylate copolymer adhesive, a lecithin gel based matrix, or a polyurethane acrylic copolymer, such as disclosed in U.S. Pat. No. 4,638,043 to Szycher et al., which is hereby incorporated by reference. Alternatively, a rate controlling membrane could be used, such as Eudragit RL-100. Further delivery mechanisms will now be disclosed.

Fragrance Delivery Systems and Mechanisms

There are several preferred methods of distributing one or more cosmetic fragrance or aromatic medicinal components throughout the strips and dilators of this invention. Such methods are herein referred to as "fragrance delivery systems" or "mechanisms." Such mechanisms include fixatives, such as floral and botanical absolutes, concretes, and resinoids, animal secretions and extracts, macrocyclic musks, polycyclic musks, nitromusks, glucoside polyols, galaxolide, ethylene brassylate, acetylhexamethyl tetralin, and like compositions disclosed in U.S. Pat. No. 5,380,707 to Barr et al. and U.S. Pat. No. 3,045,047 to Davidson et al., which are hereby incorporated by reference.

Another mechanism is a pure method wherein a liquid fragrance or medicinal component is absorbed or blended directly into the substrate, resilient member, or adhesive layers ("nasal product components") in an olfactory effective amount. See U.S. Pat. No. 3,655,129 to Seiner and U.S. Pat. No. 3,688,985 to Engel, which teach slow release fragrant films.

Other mechanisms include gels, such as gelled cellulose triacetate (U.S. Pat. No. 3,846,404 to Nichols), polyvinyl acetal resin gelled with oxygenated terpene, (U.S. Pat. No. 3,954,963 to Kudema) and polymeric carbohydrate derivatives (U.S. Pat. No. 4,067,824 to Teng et al.); said patents hereby incorporated by reference.

Another method is by using a carrier or an encapsulation, whereby the fragrance or medicinal component is contained in microcapsules, or porous carriers, such as cellulose or hydrophilic porous organic or inorganic particles, which are then mixed within a nasal product component. The carrier or encapsulation method embodiment can provide a "controlled or extended release" of the fragrance or medicinal component as well as extending the users exposure to the fragrance or medicinal component after transfer to the skin. Adhesive may be used to hold the carriers or microcapsules on a substrate prior to transfer, or they can be disposed between layers or on the exterior top surface of the preferred strips and dilators.

There are several well known types of encapsulation that may be selected to provide a controlled release of a fragrance or medication in the present invention. For example, two suitable types of encapsulation include: (a) microcapsules that rupture, by contact pressure, or by partly or completely dissolving in water or perspiration, at the point of use so that the fragrance or medicinal component is transferred to the user's skin, (b) microcapsules that continually effuse the fragrance or medicinal component without rupturing, (c) multiphase capsules, such as those disclosed in U.S. Pat. No. 3,909,444 to Anderson et al., which include a water-soluble polymeric active within a liquid permeable, water-insoluble capsule wall, for example; and (d) microcapsules which are capable of re-encapsulation, as in, for example, when perspiration evaporates, as disclosed in U.S. Pat. 5,711,941 to Behan et al., said patents hereby incorporated by reference. Behan et al. discloses a number of self-emulsifying film-forming substances, like waxy starches and modified starches sold under the trade names N-Lok and Purity Gum BE available from National Starch and Chemical Co.

Microcapsules that rupture at the point of use provide improved cold and allergy relief and shelf life, because the fragrance or medicinal component generally cannot be dissipated until the microcapsule ruptures when the therapeutic substance is transferred onto the user's nasal wall tissue. Microcapsules that continually effuse an active ingredient without rupturing, and porous carriers, also provide improved cold and allergy relief and shelf life, because the medicinal component is retained within partially open microcapsules, or within the pores of carriers, which allows the fragrance or medicinal component to continually effuse over a predetermined time period. The fragrance or medicinal component in this type of capsule or carrier dissipates at a controlled, generally more uniform rate and provides continual, longer lasting, and more reliable or defined benefits to the user. As will be understood by those skilled in the encapsulation art, suitable encapsulation technologies include coacervation, prilling, microsponging, and spray drying. Examples of preferred specific encapsulation products include those sold under the name Polyiff, as available from International Flavor and Fragrances, and IN-CAP as available from Polak Frutal Works Micro.

In a preferred embodiment of the present invention, microcapsule size may be from about 25 microns–55 microns, with a microcapsule size of about 40 microns being particularly preferred. The capsules may be coated with e.g., ureaformaldehyde or polyoxymethylene urea.

The "fill" level, defined as the weight of fragrance/weight of capsule material (shell), may be from about 60–80% by weight, with a level of about 70% by weight being particularly preferred. The viscosity of the slurry ranges from about 100–200 centipoises (cps); the microcapsules are gravure roll coated. The capsules and e.g., a gum arabic mixture may compose the slurry. In a particularly preferred embodiment, a concentration of 20% capsules by weight is present.

In the coating process, an appropriate nip gap is utilized in order to allow for the metering out of a consistent slurry of capsules and binder system. The capsule/binder is picked up by the gravure roller, with the excess removed by a doctor blade. Remaining capsule/binder is retained in the connected hexagonal grooves and "printed" onto the substrate. This procedure prevents potential "soaking" of the substrate material and minimizes the selective migration of smaller capsules onto the substrate at the expense of the larger capsules. Note that in the latter case, the slurry reservoir tends to be highly viscous and is unable to deliver capsules to the substrate.

The capsule (e.g., ureaformaldehyde or polyoxymethylene urea) size is selected so as to maximize fragrance content, and provide the optimum ease of release (i.e., rubbing versus scratching), while giving adequate strength to the system to withstand the pressures of the converting web.

The fragrance carriers employed in the compositions of the present invention preferably comprise hydrophilic particles having a diameter of from about 0.001 micron to about 50 microns, preferably from about 0.01 to about 20 microns, more preferably from about 0.1 to about 10 microns. As used herein, a "hydrophilic carrier particle" means a particle which entraps a fragrance (e.g., perfume oil or medication) in the dry (e.g., neat) nasal product and releases entrapped fragrance when the product is used, for example, when contacted by finger pressure or perspiration.

One type of inorganic carrier suitable for use in the present invention includes amorphous silica, precipitated silica, fumed silica, activated carbon, and aluminosilicates such as zeolite and alumina with a pore volume of at least 0.1 ml/g consisting of pores with a diameter between 4 and 100 A, which by their nature, are hydrophilic. Preferably, amorphous silica gel is used because of its high oil absorbency. Silica gel particles include SyloidR silicas such as Numbers: 72; 74, 221, 234; 235; 244; etc. SyloidR silicas are available from W. R. Grace & Co., Davison Chemical Division, P.O. Box 2117, Baltimore, Md. 21203. Such particles have surface areas of from about 250 to about 340 $m^2/g$; pore volumes of from about 1.1 to about 1.7 cc/g; and average particle sizes of from about 2.5 to about 6 microns. Fumed silica particles have primary particle diameters of from about 0.007 to about 0.025 micron and include Cab-O-SilR Numbers: L-90; LM-130; LM-5; M-5; PTG; MS-55; HS-5; and EH-5. Cab-O-SilR silicas are available from Cabot Corp., P.O. Box 188, Tuscola, Ill. 61953. It is preferred that there be only minimal amounts of other materials present when the fragrance is added to the silica particles to maximize absorption. It is especially preferred that only small amounts, e.g., less than about 10% of organic materials, including waxes, be present in the admixture during fragrance absorption.

Another type of carrier suitable for use in the present invention includes cyclodextrin. As used herein, the term "cyclodextrin" (CD) includes any of the known cyclodextrins such as unsubstituted cyclodextrins containing from six to twelve glucose units especially, alpha-, beta-, gamma-cyclodextrins, their derivatives, and mixtures thereof, that are capable of forming inclusion complexes with fragrance ingredients. Alpha-, beta-, and gamma-cyclodextrins can be obtained from, among others, American Maize-products Company (Amaizo), Corn Processing Division, Hammond, Ind.; and Roquette Corporation, Gurnee, Ill. There are many derivatives of cyclodextrins that are known. Representative derivatives are those disclosed in U.S. Pat. No. 3,426,011, Parmerter et al., issued Feb. 4, 1969; U.S. Pat. Nos. 3,453, 257, 3,453,258, 3,453,259 and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, U.S. Pat. No. 4,356,115, Shibanai et al., issued Oct. 26, 1982, all of said patents being incorporated herein by reference. Examples of cyclodextrin derivatives suitable for use herein are methyl-β-CD, hydroxyethyl-β-CD, and hydroxypropyl-β-CD of different degrees of substitution (D.S.), available from Amaizo and from Aldrich Chemical Company, Milwaukee, Wis. Water-soluble, e.g., perspiration dissolving, derivatives containing sugar-type, or dextrine molecules, and derivatives, are also highly desirable.

The fragrance oils, medications, carriers and capsules comprising the fragrances of the present invention can be incorporated into adhesives, substrates, and resilient members as is or they can be encapsulated in, for example, waxy materials, such as fatty acids, and then added to these nasal product components. To impregnate the fragrance within the fragrance carrier, the fragrance and the carrier are mixed together under shear conditions to provide a homogeneous mixture.

If it is desired to encapsulate the fragrance oil, medications, fragrance carrier or capsules (double encapsulation), the preferred coating materials include both water-insoluble and water-soluble materials, typically selected from waxy materials such as paraffinic waxes, microcrystalline waxes, animal waxes, vegetable waxes, saturated fatty acids and fatty alcohols having from 12 to 40 carbon atoms in their alkyl chain, and fatty esters such as fatty acid triglycerides, fatty acid esters of sorbitan and fatty acid esters of fatty alcohols, or from both water-insoluble and water soluble polymers. Typical specific suitable waxy coating materials include lauric, myristic, palmitic, stearic, arachidic and behenic acids, stearyl and behenyl alcohol, microcrystalline wax, beeswax, spermaceti wax, candelilla wax, sorbitan tristearate, sorbitan tetralaurate, tripalmitin, trimyristin and octacosane. A preferred waxy material is coconut fatty acid. Waxy materials that melt, or substantially soften, at about 98.6° F., or greater, for fragrance activation upon exercise, exertion or fever, would be ideal for nasal dilators and strips.

Examples of polymeric materials which can be used for the coating of the fragrances, medications, carriers, and microcapsules, herein are cellulose ethers, such as ethyl, propyl or butyl cellulose; cellulose esters such as cellulose acetate, propionate, butyrate or acetate-butyrate; ethylene-vinyl acetate copolymer; polyalkylene glycol such as ethylene, propylene, tetramethylene glycol; urea-formaldehyde resins, polyvinyl alcohol, polyvinyl chloride, polyvinylidene chloride, polyethylene, styrene, polypropylene, polyacrylates, polymethacrylates, polymethylmethacrylates and nylon. Such materials and their equivalents are described in greater detail in any conventional handbook of synthetic organic plastics, for example, in *Modern Plastics Encyclopaedia volume,* Vol. 62, No. 10A (for 1985–1986) at pages 768–787, published by McGraw-Hill, New York, N.Y. (October 1985), incorporated herein by reference. A preferred polymeric material is ethyl cellulose. The polymeric coating materials can be plasticized with known plasticizing agents such as phthalate, adipate and sebacate esters, polyols (e.g., ethylene glycol), tricresyl phosphate, castor oil and camphor. These polymeric coatings are preferred for the superior protection they provide.

The coating material can comprise a mixture of waxy materials and polymeric coating materials. The function of the coating which surrounds the fragrances and/or medications is to provide further improved stability, as well as to allow for dual delivery of active ingredients wherein different active ingredients can be impregnated in different delivery mechanisms to achieve: extended release, prolonged olfactory effectiveness, different neat and in-use scents or actives, and minimization of olfactory saturation.

In addition to the fragrances incorporated in coatings and microcapsules, or impregnated within a fragrance carrier, the compositions of the present invention can also optionally contain fragrances present in their liquid form (e.g., not impregnated within a fragrance microcapsule carrier). Incorporating a liquid fragrance composition into the nasal dilators and strips herein can contribute to unique fragrance impressions. For example, a nasal strip which contains both a fragrance impregnated within a fragrance carrier and a liquid fragrance can 1) give a dual fragrance impression (e.g., can exhibit different fragrance impressions for the dry (neat) strip versus the in-use strip), or 2) can optimize the fragrance impression for both the neat strip and the in-use strip.

The fragrances which can be used as neat fragrances for the nasal dilators and strips of the present invention are the same as those hereinbefore described above.

According to the dual fragrance improvements of the invention, the fragrance elements of the composition are of distinct olfactive nature and the only combination criterium resides in the harmonious effect developed by them. See U.S. Pat. No. 5,723,420 to Wei et al., hereby incorporated by reference. In a preferred embodiment of the composition which comprises two fragrance elements, one of said elements is of a heavier odor character or lower note than the other. Thus, a fragrance ingredient which develops a cooling menthol odor may harmonize well with an element having a musky, heavier odor. As a result, it could be suggested to combine the second of these ingredients in liquid or carrier form with the first in microencapsulated form. The user would then be exposed to a first impression of woody-amber scent which would be followed, upon the activation resulting from rupture of the microcapsules during perspiration, or simply from contact, with a tingling menthol sensation, for example.

In these applications, the above-mentioned embodiment of the fragrance composition wherein the micro-encapsulated ingredient is of a lighter odor character than the liquid perfuming element, turns out to be particularly advantageous for preserving the volatile high notes, such as menthol and camphor, until they are most needed. It is clear, however, that other combinations of odor characters and delivery mechanisms can be used. For example, one could use a relatively tenacious perfuming element of a baby powder character, in liquid form, combined with a micro-encapsulated element of a fresh citrus, menthol, or lavender odor, which would provide a fresh, sporty olfactive impulse following a surge of perspiration. Or, a child formulation could be employed using a cherry character, liquid benzaldehyde, with a micro-encapsulated cooling agent, WS-23 or menthol, and a micro-encapsulated analgesic and ephedrine, which are both activated by elevated body temperature or perspiration, during a fever. Another desirable combination of active agents includes a transdermally effective amount of an analgesic and anti-inflammatory agent, such as ibuprofen, with about 5–10 mg of microencapsulated or carrier impregnated aromatic menthol oil and camphor. As previously mentioned, the combination of two distinct delivery mechanisms, olfactive characters, and/or medications, is almost limitless, and preferably includes two or more fragrances and/or medications, using the same, or different, delivery mechanisms, depending on the desired effect, and end-use.

This invention also employs a fragrancing composition having fragrancing components that are not activated until they are to the skin of a human, e.g., "body activation." See U.S. Pat. Nos. 5,626,552 and 5,378,468 which teach pH activation of fragrances, and are hereby incorporated by reference. One preferred composition for achieving this result is alkaline or (if anhydrous) capable of producing an alkaline pH when in contact with water, prior to application, and includes (1) a vehicle such that when the composition is in contact with water, prior to application, the composition is at an alkaline pH; and (2) at least one potential fragrance that is at least one compound having little or no odor in the alkaline composition but which can be hydrolyzed in a lower pH environment to produce compounds having a relatively strong aroma. Upon application of the alkaline composition to the skin surface, the strong buffering capacity of the skin (the surface of which has a normal pH of 5.5–7.0) neutralizes alkalinity of the composition (lowers pH) so as to restore normal skin surface pH; the potential fragrance is then hydrolyzed at the lower pH to release the compound having relatively strong aroma. The potential fragrance or medicinal composition can be incorporated as a component of a nasal dilator strip, the fragrance or medicinal composition being released after application to the body.

Dosage

Those skilled in the art can determine the quantity of cosmetic fragrance or therapeutic substance to be applied to any given area of the substrate according to the type of fragrance or medicine to be applied and the end-use application (sports, snoring, cold-relief, adult, child, etc.). Factors to be considered include the cost of the therapeutic substance, its physical characteristics, the quantity which should be applied to the nasal skin to accomplish the particular goal of the application (e.g., soothing, protecting, relieving cold and allergy symptoms, providing a cooling sensation during a workout, etc.) and the cost and convenience of packaging. The preferred level of cosmetic fragrance or therapeutic substance is from about 0.1 mg to about 10 mg per $cm^2$ of skin depending on the substance and end use application.

Fragrances, in neat, carrier or microcapsule form, vitamins, therapeutic and medicated substances, and coated fragrances can be applied to substrates, adhesives and resilient layers of this invention by any convenient technique such as spraying, dipping, padding, or, in the case of the preferred substances, by spraying, rolling, dipping or extrusion of the oil or melted substances onto a moving web of substrate or resilient layer material.

From the foregoing, it can be realized that this invention provides improved nasal strips and dilators which include medications and fragrances having improved delivery characteristics, greater resistance to olfactory saturation, and greater shelf life and in-use effectiveness. They also reduce adhesive residue and improve upon the therapeutic delivery of aromatic medications. The dilators and methods of this invention are useful for helping individuals with deviated septums and athletes who desire more oxygen during a performance. Although various embodiments have been illustrated, this is for the purpose of describing, but not limiting the invention. Various modifications which will become apparent to one skilled in the art, are within the scope of this invention described in the attached claims.

What is claimed is:

1. A nasal strip for adhesive application to an external nasal wall tissue of a wearer, comprising: an elongated flexible I-beam shaped flexible member sized to comfortably fit across a bridge portion of a nose of said wearer, a pressure sensitive adhesive disposed on the bottom surface of said flexible layer; an aromatic substance disposed on a portion of said nasal strip in an olfactory effective amount; and a microcapsule of from about 25–55 micron for extending the olfactory effectiveness of said aromatic substance.

2. The nasal strip of claim 1, wherein said aromatic substance comprises a medication.

3. The nasal strip of claim 1, wherein said aromatic substance is substantially body activated.

4. The nasal strip of claim 3, wherein said microcapsule is gravure roll coated.

5. The nasal strip of claim 1, wherein said aromatic substance comprises a fragrance oil or essential oil.

6. The nasal strip of claim 1, wherein said aromatic substance comprises: camphor, eucalyptus oil, peppermint oil, menthol, methylsalicylate, bornyl acetate, lavender oil, citrus, an antihistamine, a decongestant, an anti-inflammatory agent, a vitamin, an analgesic, anesthetic, antipruritic, homologues, derivatives, chemical variations and combinations thereof.

7. The nasal strip of claim 1, wherein said elongated flexible layer comprises resilient means for providing a gentle expanding force to said external nasal wall tissue when said nasal strip is adhesively attached to a nose.

8. The nasal strip of claim 1, wherein said elongated flexible layer comprises a woven layer, non-woven layer, scrim, ribbon, composite, or sheet material.

9. The nasal strip of claim 1, wherein said pressure-sensitive adhesive layer is substantially separated from said aromatic substance.

10. The nasal strip of claim 1, wherein said pressure-sensitive adhesive layer and said aromatic substance are substantially separated by a separating layer therebetween.

11. The nasal strip of claim 10, wherein said separating layer comprises a portion of said elongated flexible layer.

12. The nasal strip of claim 1, wherein said aromatic substance comprises a dual fragrance delivery system for minimizing olfactory saturation.

13. The nasal strip of claim 1, wherein said aromatic substance comprises at least two fragrances notes.

14. The nasal strip of claim 1, wherein said microcapsule has a fill level of from about 60–80% by weight.

15. A nasal strip for adhesive attachment to an external nasal wall tissue of a wearer, comprising: (a) an elongated flexible I-beam shaped flexible member sized to comfortably fit across a bridge portion of a nose of said wearer, (b) a bio-compatible pressure sensitive adhesive disposed on the bottom surface of said flexible layer; (c) an aromatic substance disposed on a portion of said nasal strip in an olfactory effective amount; and (d) a microcapsule of from about 25–55 micron for minimizing olfactory saturation by said wearer.

16. The nasal strip of claim 15, wherein said microcapsule is gravure roll coated.

17. The nasal strip of claim 15, wherein said microcapsule has a fill level of from about 60–80% by weight.

\* \* \* \* \*